United States Patent [19]

Fiddian-Green

[11] Patent Number: 4,576,590

[45] Date of Patent: Mar. 18, 1986

[54] INTRALUMINAL MEMBRANE OXYGENATOR METHOD FOR A TUBULAR ORGAN OF THE GASTROINTESTINAL TRACT

[76] Inventor: Richard G. Fiddian-Green, 311 Awixa, Ann Arbor, Mich. 48104

[21] Appl. No.: 566,649

[22] Filed: Dec. 29, 1983

[51] Int. Cl.[4] ................... A61M 25/00; A61M 37/00
[52] U.S. Cl. ...................................... 604/26; 604/54; 604/96; 422/45
[58] Field of Search ............... 128/632, 635; 606/24–26, 27–29, 43–45, 51–54, 96–103; 3/1; 422/45

[56] References Cited

U.S. PATENT DOCUMENTS

| | | | |
|---|---|---|---|
| 3,505,686 | 4/1970 | Bodell | 3/1 |
| 3,512,517 | 5/1970 | Kadish et al. | 128/635 |
| 4,265,249 | 5/1981 | Schindler et al. | 128/635 |
| 4,387,711 | 6/1983 | Merry | 128/207.15 |
| 4,448,188 | 5/1984 | Loeb | 604/96 |
| 4,451,251 | 5/1984 | Osterholm | 604/26 X |

FOREIGN PATENT DOCUMENTS 1280481 11/1961 France ..................... 604/101

Primary Examiner—Dalton L. Truluck
Attorney, Agent, or Firm—Stephenson & Boller

[57] ABSTRACT

Apparatus and method for intraluminal membrane oxygenation of internal organs. A catheter having a walled chamber is introduced to dispose the chamber against the lumen of an internal organ. The wall of the chamber is of a material which is freely permeable to gases, such as oxygen and carbon dioxide, and poorly permeable to liquid. Oxygen is introduced into the catheter and perfused through the walled chamber. Oxygen passes through the wall of the chamber to the organ while carbon dioxide from the organ passes through the wall of the chamber.

6 Claims, 4 Drawing Figures

INTRALUMINAL MEMBRANE OXYGENATOR METHOD FOR A TUBULAR ORGAN OF THE GASTROINTESTINAL TRACT

BACKGROUND AND SUMMARY OF THE INVENTION

This invention relates to medical treatment apparatus and methods and more specifically is concerned with an intraluminal membrane oxygenator for use in sustaining vitality of any organ in the gastrointestinal tract.

The nature of human anatomy is such that each individual organ's vitality is sustained by the circulation of blood through the organ's vascular system. Each organ's vascular system is of course a part of the body's larger cardio-vascular system.

For any of various reasons the circulation, and hence oxygen delivery, to any given organ may become insufficient to sustain the full vitality of that organ. For example, partial occlusion of an artery may reduce blood flow to a point where the oxygen supply is insufficient. An occlusion, whether full or partial, may be due entirely to naturally occurring phenomenon or it may be in consequence of certain procedures. Regardless of the cause, reduced oxygen delivery can have potentially devastating effects on a patient.

As another example, surgical procedures, possibly not even directly related to a particular organ, may have an effect on the organ. For instance, in the case of certain vascular surgery procedures, it may be necessary to interrupt the blood flow to a given organ or organs during the course of procedures. External blood pumps may be used to supply the organ or organs during these procedures or else the procedures must be performed with sufficient rapidity that the temporary interruption of circulation to an organ will not produce grave consequences.

The present invention is directed to a novel apparatus and procedure for sustaining vitality of an internal organ in situations such as these, particularly with reference to gastrointestinal organs. With the present invention it is unnecessary to utilize external devices, such as blood pumps, in association with the vascular system. The present invention offers a procedure and apparatus which can be used at any desired time, for example, pre-operatively, during an operation, or postoperatively.

One important advantage over prior techniques and apparatus is that the invention does not directly involve the cardio-vascular system. Rather, the invention contemplates the introduction of a catheter into an organ of interest with vitality-sustaining oxygen being introduced through the catheter. The catheter comprises a tube having a walled chamber at one end. The catheter is introduced to dispose the chamber against the lumen of the organ of interest. The material of the chamber is one which is freely permeable to gas but poorly permeable to liquid. The tube contains a conduit for delivering fluid to the chamber. Oxygen is perfused through the chamber via the tube from an external source. The external source may comprise any suitable means to create an oxygen partial pressure gradient between the interior of the chamber and the lumen of the organ whereby oxygen can diffuse through the wall of the chamber and into the organ. Carbon dioxide gas generated by the organ can also diffuse through the wall of the chamber to be conveyed back through the tube for removal. The chamber and tube are so constructed and arranged as to create an axial flow along the interior of the wall of the chamber along substantially the full length of the chamber. This promotes the maximum area availability for delivering oxygen to an organ, particularly in the case where the organ is in the gastrointestinal tract. The diameter of the chamber is less than that of the organ so that the catheter does not block passage through the organ. The invention also contemplates the use of agents such as the use of a vasodialator to enhance oxygenation locally and the use of blood and/or blood substitutes for oxygen-bearing purposes.

The foregoing features, advantages and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

BRIEF DESCRIPTIOON OF THE DRAWINGS

DESCRIPTION OF THE PREFERRED EMBODIMENT

Figure 1:
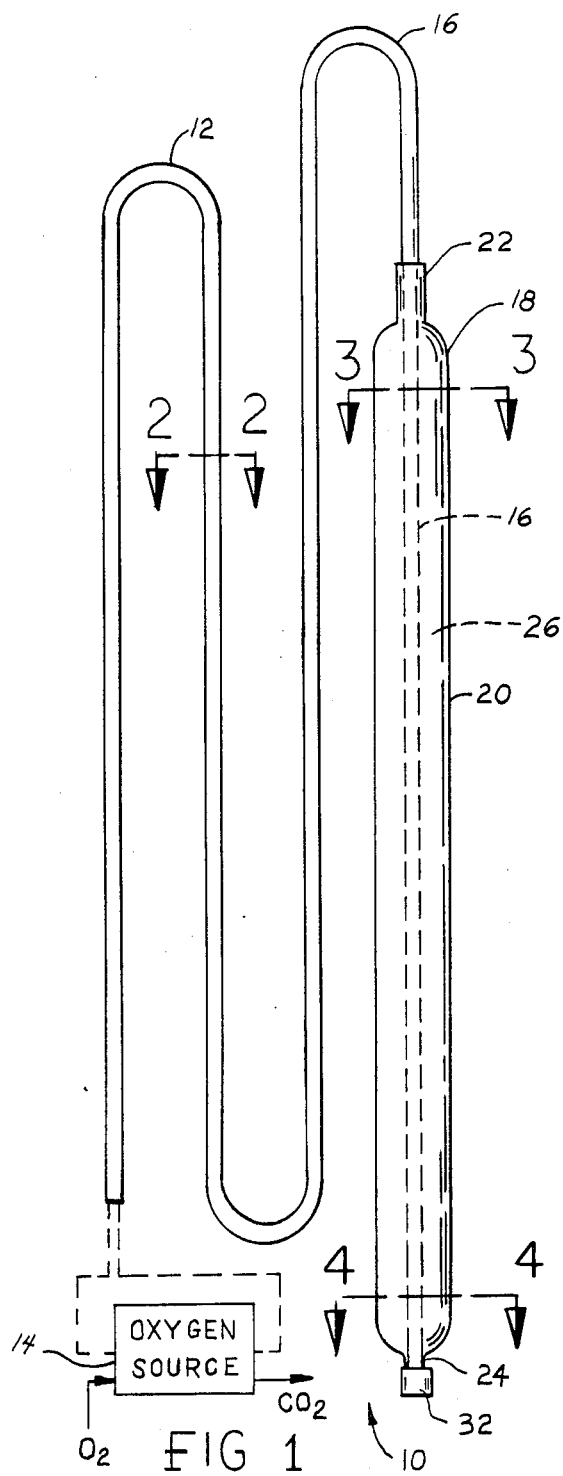
FIG. 1 is a view, partly schematic, illustrating apparatus for practice of the present invention.
Figure 2:
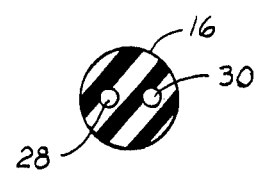
FIG. 2 is an enlarged transverse cross sectional view taken in the direction of arrows 2—2 in FIG. 1 and enlarged.

FIG. 1 illustrates a presently preferred exemplary embodiment of apparatus 10 for practice of the invention. Apparatus 10 comprises a catheter designated by the general reference number 12. Associated with catheter 12 is any suitable oxygen source designated by the general reference numeral 14.

Catheter 12 comprises a tube 16 on the distal end of which is disposed a walled chamber 18. The opposite proximal end of tube 12 is adapted for connection with apparatus 14.

Chamber 18 is provided by a tubular element having a nominal diameter greater than that of tube 16. FIG. 1 illustrates a representative shape but the invention is not limited to the particular shape or proportions illustrated. The tubular element 20 constitutes a membrane which forms chamber 18 and is fitted over the distal end of tube 16. The opposite axial ends of element 20 are closed onto the outside of tube 16 as at 22 and 24. In this way the chamber 18 defines an annular space 26 around the outside of tube 16.

Tube 16 is a soft pliable material, silicone for example, which has a circular cross sectional shape. Tube 16 is provided with a pair of axially extending conduits, or passages, 28 and 30 respectively. These extend the full length of the tube and the catheter includes any suitable closure means, for example an end closure element 32 to close off the distal end of the tube for the purpose of closing conduits 28 and 30 at that end.

Figure 3:
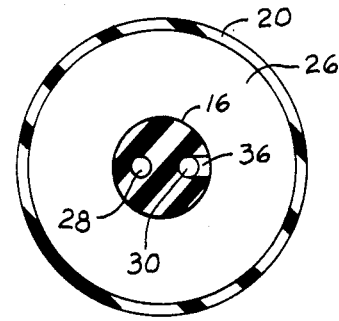
FIG. 3 is a transverse cross sectional view taken in the direction of arrows 3—3 in FIG. 1 and enlarged.
Figure 4:
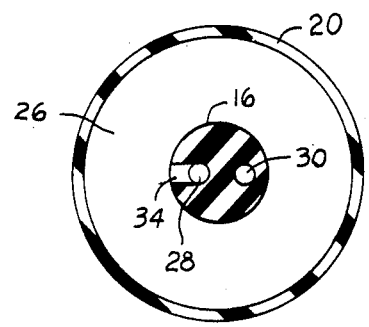
FIG. 4 is a transverse cross sectional view taken in the direction of arrows 4—4 in FIG. 1 and enlarged.

Conduits 28 and 30 are communicated with the interior chamber space 26 by means of respective apertures 34 and 36 as shown in FIGS. 4 and 3 respectively. Each aperture is provided as a transversely extending hole from the exterior of the wall of tube 16 to intercept the corresponding conduit as shown in the drawing figures.

In use oxygen is introduced into one of the two conduits and conveyed through tube 16 to exit the tube at the corresponding aperture into chamber space 26. The interior of the chamber space is thereby perfused with oxygen. The opposite aperture provides for return conveyance of gases via the other conduit through tube 16.

Hence, if oxygen is introduced into conduit 28, it will flow through that conduit, exit via aperture 34 and pass into the far distal end of chamber space 26. The flow will continue axially through the annual chamber space 26 toward the proximal end of the chamber to enter aperture 36 and subsequently pass via conduit 30 back through tube 16.

If the direction of flow were to be reversed, flow through chamber space 26 would be distally, exiting tube 16 at aperture 36, passing axially through the chamber space to re-enter tube 16 at aperture 34 for return via tube 16.

In accordance with principles of the invention, the material of tube 20 is one which is freely permeable to gas but poorly permeable to liquid, so that tube 20 is a membrane. A suitable material is polydimethylsiloxane which is freely permeable to oxygen and carbon dioxide gases. The oxygen in the catheter chamber has a partial pressure so that oxygen can diffuse through the wall of the chamber 18.

In use, catheter 12 is introduced into a patient such that chamber 18 is placed against the lumen of a hollow internal organ of interest. The elongate shape illustrated in FIG. 1 is intended for placement in the gastrointestinal tract, particularly the intestines. The placement may be made preoperatively or intraoperatively, and the catheter may remain in place even into a postoperative period.

Apparatus 14 is of any suitable configuration which is capable of perfusing oxygen through tube 16 and chamber 18 at a suitable partial pressure. For example, the apparatus may comprise a standard hospital oxygen supply giving a pressure of 760 mm.Hg. It could also alternately comprise a pump which delivers oxygen-enriched fluid. For example, the fluid may be a saline solution which is pumped by the pump through the catheter with provisions being made for oxygenating the saline solution prior to introduction into the catheter so that the fluid bears a dissolved oxygen gas at suitable partial pressure.

With the wall of chamber 18 being placed against the lumen of an internal organ, the flow of oxygen axially along the interior of the wall of tube 20 creates a condition whereby oxygen can diffuse through the wall of tube 20 and into the lumen of the organ. The diameter of chamber 26 is less than that of the organ so that the catheter does not block flow through the tract. In this way, oxygen may continue to be supplied to the organ so as to sustain its vitality under conditions which otherwise might render the organ moribund. Because the organ will also generate carbon dioxide gas as a waste product, that waste gas can diffuse from the lumen through the wall of tube 20 and into the fluid which is being conveyed through chamber space 26.

The carbon dioxide gas is conveyed from chamber space 26 with the exiting fluid flow which passes proximally through tube 16 to the proximal end. In this way not only is oxygen made available to the organ but a waste product from the organ is also removed.

Depending upon the degree of sophistication of apparatus 14 the carbon dioxide may be removed from the fluid and the fluid recirculated so as to form a closed system or otherwise the apparatus may be an open system in which the fluid which returns from tube 16 is discarded.

In order to sustain vitality of the intestine, the $PO_2$ of the oxygen introduced into chamber 26 must be high enough to create a certain gradient cross the wall of the chamber and the lumen of the organ. In the lumen of a healthy intestine the $PO_2$ is about 100 mm.Hg. If the organ becomes ischemic, this figure drops to about 60 mm.Hg. Therefore, the $PO_2$ of the fluid delivered to the catheter should certainly exceed 100 mm.Hg. At the present time the use of 760 mm.Hg. oxygen gas as the sole fluid introduced into the catheter appears to be very effective. The return flow is merely exhausted.

The invention is also preferably practiced such that the material of tube 20 is not significantly stretched, or expanded, when in use, so that blockage of the passage through the tract may be avoided.

The material of tube 20 will be permeable to molecules having molecular weights of less than about 3000. Therefore, it is also possible to use the catheter to introduce drugs, nutrients, and/or other agents having molecular weights of less than about 3000.

Certain agents enhance the effectiveness of the procedure. For example it is possible to introduce a vasodialator via the catheter to enhance the local oxygenation. It is also contemplated that blood or blood substitutes could be used in an oxygen-bearing fluid to enhance the oxygen carrying capacity.

A significant advantage of the invention is that it is unnecessary to directly involve the circulatory system for practice of the invention. Thus, the invention is different in principle from prior vascular oxygenation procedures which merely oxygenate the blood. With the invention, oxygen is made available directly at the lumen of the organ. The oxygen so delivered may be assistive of the current vascular flow, or it may be the sole source of oxygen.

The present disclosure illustrates one preferred embodiment of the invention in a form which is especially useful for the intestine. Other embodiments and forms are comtemplated within the scope of the invention. For example, the catheter could be constructed with a full nasoanal extent through the tract with oxygen being introduced at one end and the flow being discharged at the opposite end.

The invention has been shown to provide for perfusion of oxygen through a hollow internal organ of the gastrointestinal tract independently of the vascular system. The oxygen so delivered may be assistive of current blood flow to the organ or it may be the sole source. While the invention may be practiced alone, it may also be practiced in conjunction with other procedures. The perfusion is accomplished with direct oxygen delivery to the lumen of the organ in a controlled manner without blockage of the tract.

What is claimed is:

1. A method for intraluminal membrane oxygenation of a tubular internal organ of the gastrointestinal tract independently of the vascular blood supply to the organ which comprises introducing a catheter having a closed cylindrical walled chamber on a tube into the organ so as to dispose the wall of the chamber in contact with and against the lumen of the organ, said tube having an entrance to and an exit from said chamber which are disposed axially spaced apart along the length of the catheter, the wall of said chamber comprising a material which is freely permeable to gas but poorly permeable to liquid, perfusing the interior of the chamber via said tube with oxygen to create a pressure gradient between the chamber and the lumen of the organ so as to cause oxygen to diffuse through the wall of the chamber to the lumen of the organ by introducing oxygen into the tube at an external inlet, conducting the oxygen through the tube and into the chamber, thence axially through the chamber along the wall thereof, and thence from the chamber through the tube to an external outlet, and continuing the perfusion step for a sufficient time to conduct the oxygenation procedure.

2. A method as set forth in claim 1 in which oxygen is carried by a fluid and introduced into the catheter via a pumping mechanism connected with the tube.

3. A method as set forth in claim 2 in which the fluid is provided with blood or a blood substitute to enhance the oxygen bearing capacity of the fluid.

4. A method as set forth in claim 1 in which a vasodialator is also introduced via the catheter to enhance local oxygenation.

5. A method as set forth in claim 1 in which carbon dioxide which diffuses from the lumen of the organ through the wall of the chamber is conveyed with returning flow passing from the chamber through the tube.

6. A method as set forth in claim 1 in which oxygen is introduced at a $PO_2$ of about 760 mm.Hg.

* * * * *